United States Patent [19]
Hedberg et al.

[11] Patent Number: 4,722,341

[45] Date of Patent: Feb. 2, 1988

[54] ATRIUM-CONTROLLED HEART PACEMAKER

[75] Inventors: Sven-Erik Hedberg, Kungsängen; Anders Lekholm, Bromma; Anders Lindgren, Täby, all of Sweden

[73] Assignee: Siemens Aktiengesellschaft, Berlin and Munich, Fed. Rep. of Germany

[21] Appl. No.: 910,999

[22] Filed: Sep. 24, 1986

[30] Foreign Application Priority Data

Oct. 4, 1985 [DE] Fed. Rep. of Germany ....... 3535543

[51] Int. Cl.$^4$ .............................................. A61N 1/36
[52] U.S. Cl. ............................................ 128/419 PG
[58] Field of Search .................................. 128/419 PG

[56] References Cited

U.S. PATENT DOCUMENTS

| | | | |
|---|---|---|---|
| 4,363,325 | 12/1982 | Roline et al. | 128/419 PG |
| 4,467,807 | 8/1984 | Bornzin | 128/419 PG |
| 4,467,810 | 8/1984 | Vollmann | 128/419 PG |
| 4,485,818 | 12/1984 | Leckrone et al. | 128/419 PG |
| 4,527,568 | 7/1985 | Rickards | 128/419 PG |
| 4,541,430 | 9/1985 | Elmqvist et al. | 128/419 PG |
| 4,554,921 | 11/1985 | Boute et al. | 128/419 PG |
| 4,574,437 | 3/1986 | Segerstad et al. | 128/419 PG |
| 4,624,260 | 11/1986 | Baker Jr. et al. | 128/419 PG |

FOREIGN PATENT DOCUMENTS

| | | | |
|---|---|---|---|
| 2073023 | 10/1981 | United Kingdom | 128/419 PG |
| 2076655 | 12/1981 | United Kingdom | 128/419 PG |
| 2116845 | 10/1983 | United Kingdom | 128/419 PG |
| 2142539 | 1/1985 | United Kingdom | 128/419 PG |

OTHER PUBLICATIONS

"Der Diagnostische Multiprogrammierbare Physiologische Impulsgenerator 674".

Primary Examiner—William E. Kamm
Assistant Examiner—Timothy Keegan
Attorney, Agent, or Firm—Hill, Van Santen, Steadman & Simpson

[57] ABSTRACT

An atrium controlled heart pacemaker has a switching stage which is controlled in dependence upon the appearance of atrial signals. The switching stage switches the heart pacemaker to a VVI mode for a predetermined number of stimulation pulses or natural ventricular events, or a predetermined time, upon the appearance of at least one atrial signal before a selected time limit. The time limit is derived from the difference between a smallest synchronous interval and the AV delay.

7 Claims, 3 Drawing Figures

ATRIUM-CONTROLLED HEART PACEMAKER

BACKGROUND OF THE INVENTION

The present invention relates to atrium-controlled heart pacemakers. In such pacemakers, generation of a ventricular stimulation pulse occurs after a delay time following the appearance of an atrial signal.

In heart pacemakers of this type, the stimulation frequency can vary within a relatively wide range of, for example, 50 through 150 pulses per minute. An atrium-controlled pacemaker contains a limiting stage which defines the highest pulse rate. The heart pacemaker thus does not always function completely reliably, particularly when an atrial signal appears within certain time limits relative to a stimulation pulse in the ventricle.

It is an object of the present invention to provide an atrium-controlled heart pacemaker which guarantees reliable operation independently of the chronological appearance of an atrial signal with respect to a ventricular stimulation pulse.

The above object is achieved in accordance with the principles of the present invention by a heart pacemaker having a switching stage controlled dependent on the appearance of atrial signals, the switching stage switching the pacemaker to ventricular inhibited (VVI) mode for a predetermined plurality of stimulation pulses or natural ventricular events upon the appearance of at least one atrial signal occurring before a selected time, the selected time being derived from the difference between a smallest synchronous signal and the AV delay.

In a pacemaker constructed in accordance with the principles of the present invention, reliable operation is further guaranteed upon the appearance of atrial signals within an interval which is smaller than the smallest interval defined by the highest allowable stimulation pulse rate.

When an atrial signal appears within the smallest programmed interval between two ventricular stimulation pulses which has been reduced by the AV delay time, the pacemaker can be switched for generating either a low pulse rate or a high pulse rate in the VVI mode. A predetermined number of ventricular stimulation pulses will be emitted in any event, the predetermined number being, for example, between one and sixteen pulses. The pulse rate supplied in the VVI mode, accordingly, is between the base rate and the highest synchronous pulse rate of the pacemaker.

In the case, wherein an atrial signal appears within the interference interval, the pacemaker can be switched to a prescribed low pulse rate which can be one of the programmed base rates. Because this operating mode is intended to protect against external interference, the pulse rate should accordingly be at least approximately equal to the base rate.

An additional feature of operation with the highest synchronous pulse rate is the capability of protecting the heart pacemaker against tachycardia induced by the pacemaker. This is guarded against because the high VVI pulse rate is programmed to be slightly lower than the highest synchronous pulse rate. Because tachycardia induced by the heart pacemaker results in the heart pacemaker stimulating the heart with the highest synchronous pulse rate, the selected difference between the highest synchronous pulse rate and the high VVI pulse rate makes tachycardia induced by the heart pacemaker impossible.

DESCRIPTION OF THE PREFERRED EMBODIMENTS

Figure 1:
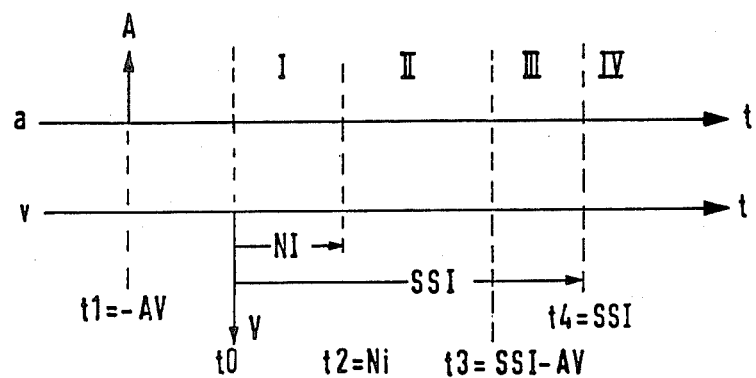
FIG. 1 is a graph showing atrial and ventricular signals during operation of a pacemaker constructed in accordance with the principles of the present invention.

A graph for explaining the operation of the heart pacemaker described herein is shown in FIG. 1. Two coincident time axes are shown horizontally in FIG. 1, the top axis "a" representing atrial events and the bottom axis "v" representing ventricular events. The ventricular events may be stimulation pulses or natural ventricular activity. An atrial signal A is shown on the axis "a" and a ventricular signal V following with a delay time AV is shown on the axis "v." The point in time t4 defines the end of the smallest interval between two stimulation pulses, and thus the highest synchronous pulse rate or, the smallest synchronous signal interval SSI. The interval between t0 at v and t4 is divided into three regions I, II and III, and the time following the point in time t4 is referenced IV.

The interval between t3=t4−AV and t0 is divided into the two regions I and II by a point in time t2. The point in time t2 defines the programmed interference interval NI.

The heart pacemaker operating in accordance with the sequence shown in FIG. 1 includes a program memory for ventricular inhibited operation (VVI mode) with a selected low pulse rate or a selected high pulse rate. Switching to the VVI mode with one of the two available pulse rates is undertaken by a switching stage in accordance with the chronological appearance of atrial signals. The operation may be summarized as follows:

| Appearance of an atrial signal in: | Results In: |
|---|---|
| Region I | switching to VVI mode at a low pulse rate for at least one interval. |
| Region II | switching to VVI mode for a prescribed plurality of stimulation pulses or natural ventricular events, or for a prescribed time, a pre-programmed high pulse rate. |
| Regions III, IV | normal atrial-controlled operation (DDD mode). |

Figure 2:
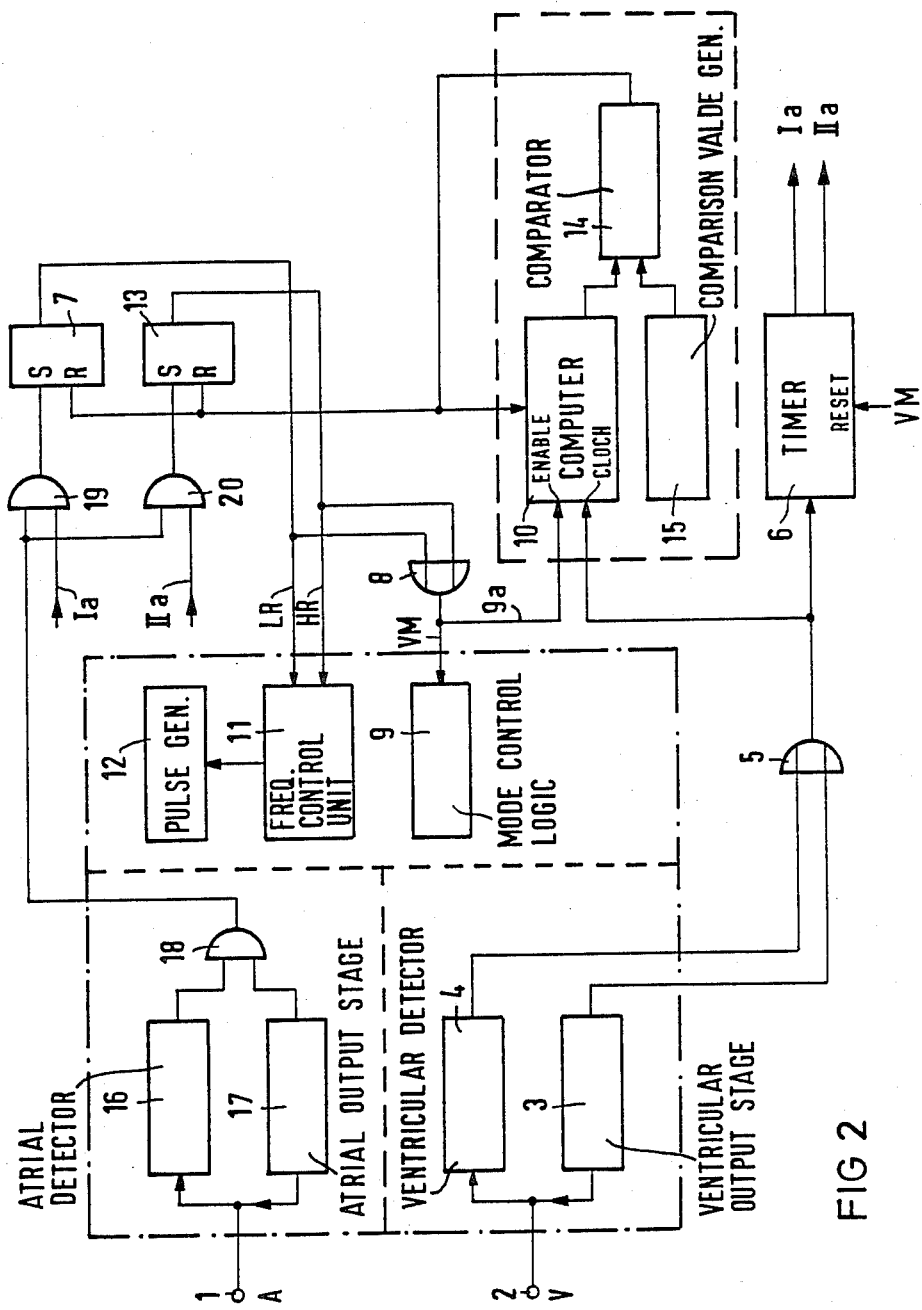
FIG. 2 is a schematic block diagram of a heart pacemaker constructed in accordance with the principles of the present invention.

In the schematic diagram shown in FIG. 2, atrial signals are supplied to a terminal 1 and ventricular signals are supplied to a terminal 2, the terminal 2 also being used to supply ventricular stimulating pulses to the heart. Pulses from a ventricular output stage and a ventricular detector proceed through an OR gate 5 to start a timer 6. The timer 6 has two outputs Ia and IIa, which correspond to the regions I and II in FIG. 1.

An atrial signal which occurs when the output Ia of the timer 6 is at a logic "1" state sets a flip-flop 7, whose output signal is forwarded through an OR gate 8 to mode control logic 9. The mode control logic 9 initiates a mode change from normal DDD operation to the VVI mode. The same signal causes a logic "1" at the enabling input of a computer 10, so that the timer 6 is reset and remains at a logic "0."

A basic frequency control unit 11 also receives the output signal of the flip-flop 7, which causes the pulse generator 12 to generate pulses at a predetermined low frequency. The pulse generator 12 and the mode control logic 9 are connected to the pacemaker outputs in a known manner, which is not described in greater detail nor shown in detail in the drawings.

If an atrial signal occurs during the region II, a flip-flop 13 is switched to a logic "1" status. The output signal of the flip-flop 13 proceeds through the OR gate 8 to the mode control logic 9, which again selects the VVI mode. The computer 10 is activated by a suitable signal on input line 9a. The basic frequency control 11 is now controlled by the output signal of the flip-flop 13, and the basic frequency of the pacemaker is thereby caused to be a predetermined higher value. When a logic "1" is supplied on input line 9a of the computer 10, the computer 10 begins to calculate at each stimulation pulse or at each detection of a natural heart event in the ventricle. A predetermined number of ventricular stimulation pulses and/or natural activities of the heart are prescribed, during which the pacemaker will operate in the VVI mode.

A comparator 14 compares the content of the computer 10 to a prescribed number of pulses n of a comparison value generator 15. When the contents of the computer 10 and the generator 15 are identical, the comparator emits an output signal which resets the flip-flops 7 and 13 as well as the computer 10. This signal ceases as soon as the flip-flops 7 and 13 are reset. The output of the OR gate to the mode control logic 9 also then changes to zero. The mode control logic 9 thus causes a return to the DDD mode in a controlled manner.

Acquisition of the atrial signal is undertaken by a detector 16 to which an output stage 17 is allocated, and which is followed by an OR gate 18. The OR gate 18 controls the flip-flops 7 and 13 through two AND gates 19 and 20.

Figure 3:
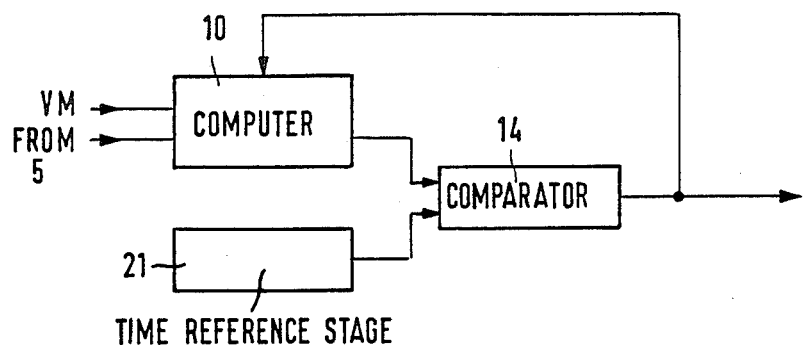
FIG. 3 is a schematic block diagram of a further embodiment of a portion of the circuit shown in FIG. 2.

A modification of a portion of the circuit of FIG. 2 is shown in FIG. 3. In the embodiment of FIG. 3, one input of the comparator 14 is connected to a time reference stage 21. When a logic "1" is supplied to the enable input of the computer 10, the computer 10 is clocked by a periodic clock signal. The time thus determined by the time reference stage 21 prescribes the length during which the pacemaker will remain in the VVI mode, before returning to normal DDD operation.

Although modifications and changes may be suggested by those skilled in the art it is the intention of the inventors to embody within the patent warranted hereon all changes and modifications as reasonably and properly come within the scope of their contribution to the art.

We claim as our invention:

1. An atrium-controlled heart pacemaker operable with an AV delay and having a highest synchronous pulse frequency which defines a smallest synchronous interval comprising:
    means for sensing atrial events in said heart;
    means for sensing ventricular events in said heart;
    means for normally supplying ventricular stimulation pulses to said heart in a first mode of operation, said means for supplying including mode control logic;
    means for switching said means for supplying ventricular pulses to a second mode of operation for a predetermined period upon the occurrence of a sensed atrial event within a selected time following a ventricular event, said selected time being the difference between said smallest synchronous interval and said AV delay; and
    said means for switching including a timer connected to said means for sensing ventricular events and to said means for supplying ventricular pulses, said timer generating an output signal commencing with a pulsed or sensed natural ventricular event and ending at said selected time, a flip-flop having an output connected to said mode control logic, a logic gate having inputs respectively connected to said means for sensing an atrial event and to the output of said timer and having an output connected to said flip-flop, said logic gate causing said flip-flop to change from a rest status if an atrial event occurs during said selected time thereby causing said mode control logic to change from said first mode to said second mode, and means for resetting said flip-flop at the end of said predetermined period.

2. A heart pacemaker as claimed in claim 1, further comprising means for supplying atrial stimulation pulses to said heart, wherein said first mode is a DDD mode, and further comprising means for operating said means for supplying ventricular pulses and said means for supplying atrial pulses in combination in said DDD mode.

3. A heart pacemaker as claimed in claim 1, wherein said second mode is a VVI mode, and further comprising means for operating said means for supplying ventricular pulses in said VVI mode.

4. A heart pacemaker as claimed in claim 1, wherein said predetermined period corresponds to a selected total of natural or pulsed ventricular events.

5. An atrium-controlled heart pacemaker operable with an AV delay and having a highest synchronous pulse frequency which defines a smallest synchronous interval comprising:
    means for sensing atrial events in said heart;
    means for sensing ventricular events in said heart;
    means for normally supplying ventricular stimulation pulses to said heart in a first mode of operation;
    means for switching said means for supplying ventricular pulses to a second mode of operation for a predetermined period upon the occurrence of a sensed atrial event within a selected time following a ventricular event, said selected time being the difference between said smallest synchronous interval and said AV delay;
    said means for supplying ventricular pulses including mode control logic, a pulse generator, and a frequency control unit for said pulse generator for operating said pulse generator in said second mode at a low pulse frequency upon the occurrence of a signal at a first input of said control unit or at a high pulse frequency upon the occurrence of a signal at a second input of said control unit, and said means for switching including;
    a timer connected to said means for sensing ventricular events and to said means for supplying ventricular pulses, said timer commencing timing upon the occurrence of a pulsed or sensed natural ventricular event and generating a first output signal ending at said further selected time at a first output and thereafter generating a second output signal ending at said selected time at a second output;

a first flip-flop having an output connected to said first input of said control unit;

a second flip-flop having an output connected to said second input of said control unit;

a first logic gates having inputs respectively connected to said means for sensing atrial events and to said first output of said timer, said first logic gate causing said first flip-flop to change from a rest status thereby causing said frequency control unit to operate said pulse generator at said low pulse frequency;

a second logic gate having inputs respectively connected to said means for sensing atrial events and to said second output of said timer, said second logic gate causing said second flip-flop to change from a rest status thereby causing said frequency control unit to operate said pulse generator at said high pulse frequency;

a third logic gate having inputs respectively connected to the outputs of said first and second flip-flops and an output connected to said mode control logic, said third logic gate generating a signal causing said mode control logic to change from said first to said second mode upon a change from said rest status of either said first or second flip-flops; and means for resetting said flip-flops at the end of said predetermined period.

6. An atrium-controlled heart pacemaker operable with an AV delay and having a highest synchronous pulse frequency which defines a smallest synchronous interval comprising:

means for sensing atrial events in said heart;

means for supplying ventricular stimulation pulses to said heart;

means for supplying atrial stimultion pulses to said heart;

means for dividing said smallest synchronous interval into first, second and third chronologically successive regions;

means connected to said means for sensing atrial events, said means for sensing ventricular events, said means for supplying ventricular pulses and said means for dividing for operating said pacemaker in a low frequency VVI mode for a predetermined period following a ventricular event if an atrial event is sensed in said first region, operating said pacemaker in a high frequency VVI mode for said predetermined period following a ventricular event if an atrial event is sensed in said second region, and continuously operating said pacemaker in a DDD mode if an atrial event is sensed in said third region or thereafter.

7. A heart pacemaker as claimed in claim 6, wherein said second region ends at a time defined by the smallest synchronous interval minus the AV delay.

* * * * *